US009193983B2

(12) United States Patent
Schiestl et al.

(10) Patent No.: US 9,193,983 B2
(45) Date of Patent: Nov. 24, 2015

(54) ASSAYS FOR MUTAGENESIS DETECTION

(75) Inventors: Robert H. Schiestl, Encino, CA (US);
Nikos Hontzeas, Los Angeles, CA (US);
Kurt M. Hafer, Los Angeles, CA (US);
Jiri Aubrecht, Stonington, CT (US);
Yelena O. Rivina, Sherman Oaks, CA (US)

(73) Assignee: The Regents of the University of California, Oakland, CA (US)

( * ) Notice: Subject to any disclaimer, the term of this patent is extended or adjusted under 35 U.S.C. 154(b) by 693 days.

(21) Appl. No.: 12/627,985

(22) Filed: Nov. 30, 2009
(Under 37 CFR 1.47)

(65) Prior Publication Data

US 2011/0065131 A1   Mar. 17, 2011

Related U.S. Application Data

(63) Continuation-in-part of application No. PCT/US2008/064985, filed on May 28, 2008.

(60) Provisional application No. 60/940,633, filed on May 29, 2007.

(51) Int. Cl.
*C12Q 1/02* (2006.01)
*G01N 33/50* (2006.01)

(52) U.S. Cl.
CPC ............ *C12Q 1/025* (2013.01); *G01N 33/5014* (2013.01); *G01N 33/5017* (2013.01); *G01N 33/5076* (2013.01); *G01N 33/5079* (2013.01)

(58) Field of Classification Search
None
See application file for complete search history.

(56) References Cited

U.S. PATENT DOCUMENTS

| 4,997,757 | A  | 3/1991  | Schiestl |
| 5,273,880 | A  | 12/1993 | Schiestl |
| 5,762,908 | A  | 6/1998  | Schiestl |
| 6,264,915 | B1 | 7/2001  | Schiestl |
| 2005/0148007 | A1 | 7/2005 | Aubrecht et al. |

FOREIGN PATENT DOCUMENTS

WO   2008150802 A1   12/2008

OTHER PUBLICATIONS

Sommer et al. Journal of Food Protection, vol. 67, No. 6, 2004, pp. 1293-1298.*
Stowe et al. Journal of Microbiological Methods 22 (1995) 283-292.*
Sommers et al. In vitro toxicology, vol. 8, No. 1, 1995 p. 37-47.*
Mosmann, "Rapid colorimetric assay for cellular growth and survival: application to proliferation and cytotoxicity assays", J. Immunol. Methods, 1983, vol. 65, pp. 55-63.
Young, Lee W., International Search Report and Written Opinion, Date of Mailing of Report Oct. 2, 2008; International Application No. PCT/U52008/064985.
Lindner, Nora, International Preliminary Report on Patentability and Written Opinion; Date of Issuance of Report Dec. 1, 2009; International Application No. PCT/US2008/064985.
Lindner, Nora, International Preliminary Examination Report on Patentability and Written Opinion, Date of Mailing of Report Jun. 14, 2012; International Application No. PCT/US2010/058425.
Hontzeas, N. et al., "Development of a Microtiter Plate Version of the Yeast DEL Assay Amendable to High-throughput Toxicity Screening of Chemical Libraries," Mutation Research, 634:228-234 (2007).
Josephy, P. David, "The *Escherichia colt lacZ* Reversion Mutagenicity Assay," Mutuation Research, 455:71-80 (2000).
Lanlan, Y. et al., "Construction of *Kluyveromyces lactis leu2* Mutants by One-step Gene Disruption," HEREDITAS (Bejing) 16(3):28-32 (1994). Abstract Only.
Malich, G. et al., "The Sensitivity and Specificity of the MTS Tetrazolium Assay for Detecting the In Vitro Cytotoxicity of 20 Chemicals Using Human Cell Lines," Toxicology, 124:179-192 (1997).
Mosmann, T., "Rapid Colorimetric Assay for Cellular Growth and Survival: Application to Proliferation and Cytotoxicity Assays," J. of Immun. Methods, 65:55-63 (1983).
Sanchez, Norma Silvia, et al., "Using Yeast to Easily Determine Mitochondrial Functionality with 1-(4,5-Dimethylthiazol-2-y1)-3,5-diphenyltetrazolium Bromide (MTT) Assay," Biochemistry and Molecular Biology Education, 34(3):209-212 (2006).
Schiestl, Robert H. et al., "Nonmutagenic Carcinogens Induce Intrachromosomal Recombination in Dividing Yeast Cells", Environmental Health Prospectives, 101(Suppl. 5):179-184 (1993).

* cited by examiner

*Primary Examiner* — Oluwatosin Ogunbiyi
(74) *Attorney, Agent, or Firm* — Foley Hoag LLP

(57) ABSTRACT

The disclosure provides methods, systems, and kits for assaying an agent for mutagenic properties. The methods systems and kits utilize a DEL selectable marker and a colorimetric detection systems. Also included are methods systems and kits that utilize a DEL selectable marker and a regent that detects mitochondrial activity.

18 Claims, 3 Drawing Sheets

ASSAYS FOR MUTAGENESIS DETECTION

CROSS REFERENCE TO RELATED APPLICATIONS

This patent application is a continuation-in-part of International Application No. PCT/US08/64985, filed May 28, 2008, which application claims the benefit of U.S. Provisional Patent Application No. 60/940,633 filed on May 29, 2007, and incorporated herein by reference in its entirety.

STATEMENT REGARDING FEDERALLY SPONSORED RESEARCH

The invention was made with Government support under Grant No. AI067769 awarded by the National Institutes of Health. The government has certain rights in the invention.

FIELD OF THE INVENTION

The invention relates to mutagenesis assays and to cells and kits useful therein.

BACKGROUND

It is generally accepted that the mutagenic potential of a chemical agent is roughly proportional to the agent's carcinogenic potential. An early determination of whether a particular agent presents a hazard of mutagenicity is fundamental to the development of products for the chemical, cosmetic, food additive and pharmaceutical industries.

Mutagens are agents that cause an increase in the rate of mutation, i.e. detectable and heritable structural changes in the genetic material of an organism. Such changes may include the addition or deletion of a whole chromosome, a structural change to a chromosomes (e.g., a translocation) and a structural change to a portion of the genomic sequence (e.g., point mutations, mutations to multiple sequential nucleotides and deletions of portions of the genomic sequence). Because genetic changes can damage or otherwise interfere with the action of genes, mutagens are characterized as genotoxins, i.e. agents that are toxic to genes.

SUMMARY

The disclosure provides a nucleic acid construct comprising an auxotrophic gene disrupted by a colorigenic enzyme gene which is disrupted by a polynucleotide encoding a selectable marker. In one embodiment, the auxotrophic gene comprises a His3 gene. In another embodiment, the selectable marker comprise a Ura3 gene. In yet a further embodiment, the construct comprises a plasmid. In one embodiment, the construct is recombinantly introduced into a host cell genome. In yet another embodiment, the colorigenic enzyme gene comprise LacZ. In yet a further embodiment, the construct comprises a sequence selected from the group consisting of: (a) SEQ ID NO:1; (b) a sequence that is 95% identical to SEQ ID NO:1; (c) a complement of (a) or (b); and (d) a sequence of (a), (b) or (c), wherein T can be U.

The disclosure also provides a host cell recombinantly engineered to contain the construct above. In one embodiment, the host cell is a eukaryotic cell. In a further embodiment, the host cell is *Saccharomyces cerevisiae*.

The disclosure also provides a method of characterizing an agent as mutagenic comprising contacting a host cell comprising the construct above with an agent and measuring the activity of beta-galactosidase, wherein an increase in beta-galactosidase activity compared to a control is indicative of an agent having mutagenic potential.

The disclosure provides a method for characterizing a test agent, comprising: treating a eukaryotic cell comprising a DEL selection marker with a test agent; and measuring mitochondrial activity following treating the eukaryotic cell with the test agent. In one aspect, the disclosure uses an MTT or MTS reagent to detect mitochondrial activity. In yet another aspect, the cell is a yeast cell.

The disclosure provides a method for characterizing a test agent, comprising: providing a eukaryotic cell culture comprising a DEL selection marker; treating the eukaryotic cell culture with or without a test agent; measuring the mitochondrial activity of a treated portion of the cell culture in the presence of a suitable selection medium; and measuring the mitochondrial activity of an untreated portion of the cell culture in the presence of said selection medium. In one aspect, the disclosure uses an MTT or MTS reagent to detect mitochondrial activity. In yet another aspect, the cell is a yeast cell.

The disclosure also provides a kit comprising a cell comprising a DEL selection marker and a mitochondrial activity detection agent.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
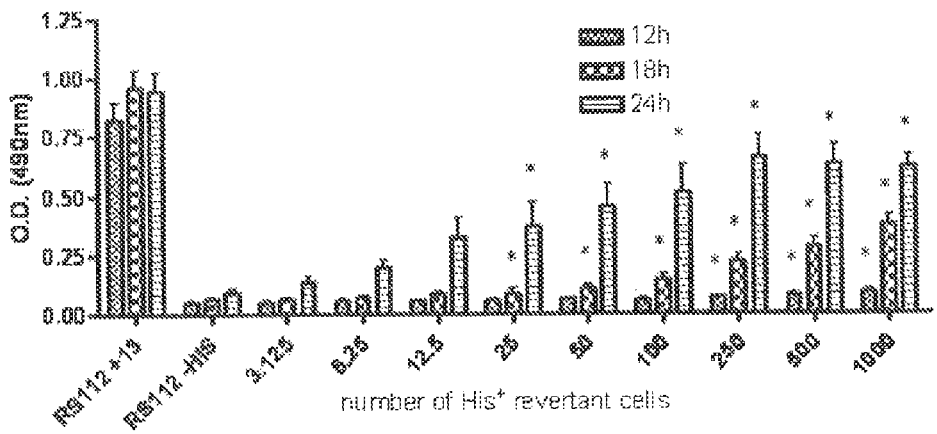
FIG. 1 shows the DEL assay was simulated by adding different dilutions of RS112 His$^+$ revertants to 100,000 background RS112 cells in –His media. 12, 18, and 24 hour time points are charted. At 12 hours, RS112 His$^+$ additions corresponding to 25, 50, and 100 DEL events per 10,000 cells were discernibly significant. By both 18 and 24 hours, as few as 2.5 DEL events per 10,000 cells were significantly detectable. Yet at 24 hours, whilst 25-1000 RS112 cells are still significantly different than background, growth in –His media becomes saturated and response pattern is lost. The experiment was carried out using at least 6 repeats for each treatment group, and the results are presented as means±SD. Significance* ($p<0.05$).

As used herein and in the appended claims, the singular forms "a," "and," and "the" include plural referents unless the context clearly dictates otherwise. Thus, for example, reference to "a cell" includes a plurality of such cells and reference to "the agent" includes reference to one or more agents known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The publications discussed above and throughout the text are provided solely for their disclosure prior to the filing date of the present application. Nothing herein is to be construed as an admission that the inventors are not entitled to antedate such disclosure by virtue of prior disclosure.

Originally developed as an instrument to study the mechanisms of DNA recombination and repair the DEL Assay has stood the test of time and has proven itself to be an invaluable tool in a variety of research fields—Cancer, Toxicology, Environmental Sciences, Public Health, Radiobiology, and Pharmacology. While it remains an excellent model for the study of DNA recombination/repair pathways and long term genetic instability, early on the DEL Assay has shown to be very sensitive and accurate in the detection of carcinogenicity of agents that were missed by the well-accepted *Salmonella* assay (Ames). DEL Assay recognizes 92% of the known carcinogens while the Ames Assay only 60%. The DEL Assay effectively predicts genotoxic and cytotoxic properties of various agents and stressors with very distinct mechanisms of mutagenic activity. It can detect agents that induce genetic changes via oxidative stress, single and double DNA breaks, clastogenic activity, UV-induced base dimerization, DNA crosslinking, DNA stacking, and low LET Gamma radiation.

The DEL Assay has also been recently used to investigate internal oxidative stress inducer NHO and demonstrated an ability to detect oxidative stress neutralizers such as NAC (N-acetylamine). HNO is genotoxic but its mechanism is not well understood. There are many possible mechanisms by which HNO can attack DNA. Since HNO is electrophilic, it may react with exocyclic amine groups on DNA bases and through a series of subsequent reactions form a deaminated product. Alternatively, HNO may induce radical chemistry through O(2)-dependent (or possibly O(2)-independent) chemistry. In cell free systems, experiments have shown that HNO does react with DNA, resulting in base oxidation and strand cleavage. A whole-cell system in the yeast *Saccharomyces cerevisiae* was used to study the mechanism of HNO induced DNA damage with Angeli's salt as HNO donor. The yeast DEL assay provided a measure of intrachromosomal recombination leading to DNA deletions. HNO was a potent inducer of DNA deletions and recombination but it was negative for induction of point mutations. This suggests that HNO causes DNA strand breaks rather than base damage. Genotoxicity was observed under aerobic and anaerobic conditions and NAC protected against HNO induced DNA deletions. Since HNO is genotoxic under anaerobic conditions, NAC probably protected against radicals generated by HNO independent of oxygen.

Since the DEL assay is highly inducible by DNA double strand breaks, a study was developed to examine the utility of the DEL assay for detecting clastogens. Ten model compounds, with varied mechanisms of genotoxicity, were examined for their effect on the frequency of DNA deletions with the DEL assay. The compounds tested were: actinomycin D, camptothecin, methotrexate and 5-fluorodeoxyuridine, which are anticancer agents, noscapine and furosemide are therapeutics, acridine, methyl acrylate and resorcinol are industrial chemicals and diazinon is an insecticide. The in vitro micronucleus assay (IVMN) in CHO cells, a commonly used tool for detection of clastogens, was performed on the same compounds and the results of the two assays were compared. The results of the study show that there is 70% concordance in the presence of metabolic activation (rat liver S9) and 80% concordance in the absence of metabolic activation between the DEL assay and the standard in vitro micronucleus assay. The lack of cytotoxicity observed for four of the ten compounds examined indicates limited diffusion of lipophilic compounds across the yeast cell wall. Thus, the development of a more permeable yeast tester strain is expected to greatly improve concordance of the DEL assay with the IVMN assay. The yeast DEL assay is inexpensive, amenable to automation and requires less expertise to perform than the IVMN. Thus, it has a strong potential as a robust, fast and economical screen for detecting clastogens in vitro.

The DEL Assay has also found applications outside of a pure research setting in the fields of Environmental Health Sciences and Public Health laboratories. DEL Assay has been used to shown mutagenic consequences of tap water chlorination, diesel exhaust, and benzene exposures.

The DEL Assay has been adapted to a high throughput format (HTS) to ease the process of detection of genotoxicity and cytotoxicity in compounds of interest and as a means to screen chemical libraries for radiation-induced damage modifiers. The disclosure describes a modification of the yeast DEL assay into a colorimetric assay using the MTS tetrazolium compound (3-(4,5-dimethylthiazol-2-yl)-5-(3-carboxymethoxyphenyl)-2-(4-sulfophenyl)-2H-tetrazolium, inner salt) to allow for efficient detection of chemical genotoxicity. It has been micro-scaled and can be performed in 96- or 384-well format. Chemicals previously characterized with the DEL plate-based assay were utilized to test the new well-based format, and a group of cross-linking agents, previously uncharacterized by the DEL assay, were scored for genotoxicity using this new assay format. These compounds induced a range of genotoxicity detectable with the well-based DEL assay, and a lack of sensitivity was found only at extremely low genotoxic levels determined by the plate-based DEL assay. Radiation modulating agents identified by the DEL HTS—radioprotectors, radiomitigators, and radiosensitizers—can be translated into higher Eukaryotic cell in vitro models and potentially whole organisms. Recently, the compounds identified by the DEL HTS as having radiation protection/mitigation activity have been tested in animals and have shown great effects in mitigating lethal radiation exposure damage in mice and are being further developed into a drug therapy.

There is yet another pharmacological application of the DEL Assay: a screen for genotoxic pharmaceutical impurities left as by-products in drug manufacturing. Drug synthesis and/or formulation can generate genotoxic impurities. For instance, strong acid/alcohol interactions during the process of drug salt formation produce alkylating agents such as alkyl halides and alkyl esters of alkyl sulfonic acids. The genotoxicity of a few classic alkylating agents such as methyl and ethyl methanesulfonate have been previously well characterized, whereas the majority of compounds from this class have only been tested in the *Salmonella* reversion assay. Therefore, the disclosure provides methods and compositions useful to investigate clastogenicity and DEL recombination profiles of 22 halogenated alkanes and alkylesters of sulfuric and alkane-, aryl-sulfonic acids using a battery of cellular and molecular assays was performed. DEL Assay in *S. cerevisiae* provided a measure of DNA deletions. Methylating agents were most potent in the DEL assay and the alkyl chlorides evaluated in the study were negative. In summary, this study contributes to a better understanding of the genotoxic properties of common alkyl halides and alkyl esters with alkylating activity and might provide guidance for managing risk of genotoxic process-related impurities of drug substances and products.

Figure 3:
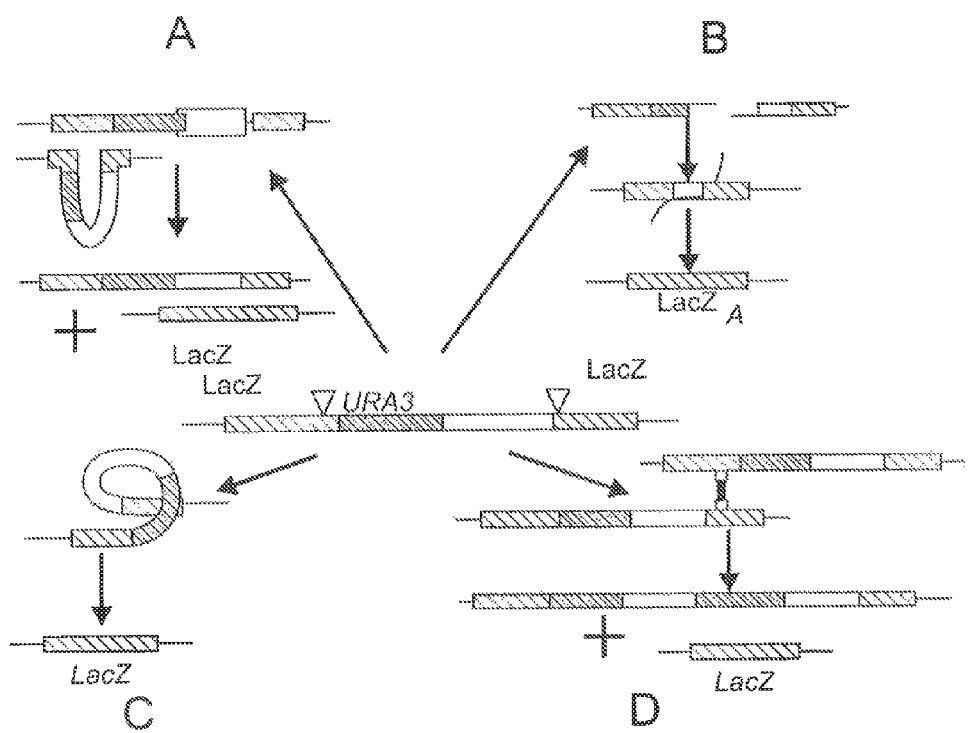
FIG. 3A-D is a schematic showing the structure and possible mechanisms for reversion of the yeast intrachromosomal recombination (DEL) system. A: Sister chromatid conversion; B: single strand annealing; C: intrachromosomal crossing over; D: unequal sister chromatid exchange.

In addition to the colorgenic DEL Assay of the disclosure, yet another DEL Assay is provided by the disclosure. The LacZ DEL Assay described herein capitalizes on the same concept of a disrupted gene that undergoes recombination in the presence of a mutagenic compound or event (X-ray, gamma ray, etc). LacZ fused to a galactose promoter was inserted into a growth required gene (e.g., a growth selectable marker such as the genomic His3 locus and disrupted by a plasmid with an internal fragment of the Gal-LacZ construct. The result is two copies of the Gal-LacZ construct with terminal deletions with a disruption by URA3 gene (for selection) that revert to a functional Gal-LacZ phenotype upon exposure to genotoxic compounds and events (see, e.g., FIG. 3). Detection of the functional Gal-LacZ phenotype is possible with the addition of bromo-chloro-indolyl-galactopyranoside (X-gal) substrate to the media and a brief incubation period in the dark. Results are read as the proportion of colonies turning blue (indicating genotoxicity/carcinogenicity) in the presence of the compound to the spontaneous reversions. In an HTS adaptation a spectrophotometer will be used to indicate differences in absorbencies.

The LacZ DEL construct has multiple advantages over the classical DEL construct. First of all, it will provide an even more sensitive tool for the detection of genotoxicity as the gene construct is larger. Second, the detection of genotoxicity will be six times faster as the new assay will not be based on growth (at least 18 hrs of growth) but on a change of colony color (from white to blue in less then 3 hrs). Third, the assay will be portable and will allow for a genotoxic screen in the field. Lastly, it will be amenable to an HTS format and will be more cost-efficient as the MTS indicator substrate is useful but more expensive. In addition to the above mentioned advantages in cost and time reduction the new DEL-LacZ construct provides a tool for exploring the mechanism of DNA repair through various pathways. For example, the DEL-LacZ construct enables us to differentiate between those clones that have undergone a recombination event through the non-homologous end joining (NHEJ) pathways from those that have undergone a homologous recombination event. Such is possible to observe because if the selected clone has undergone a homologous recombination and lost the URA3 interruption sequence it would turn blue in the presence of the X-gal substrate and would not be able to survive in the media with FOA (5-fluoro-orotic acid, that in the presence of an intact URA3 gene is converted to a toxic 5-fluorouracil). If however, the selected clone would remain white but lose the URA3 gene this would indicate a non-homologous end joining event.

"Bioluminescence" means light emission in a living cell wherein the light emission is dependent upon and responsive to metabolic activity.

"Bioluminescent marker" means a nucleotide sequence that, when incorporated into a cell and expressed, causes bioluminescence during metabolic activity of the cell.

The term "colorimetric" refers to a composition that generates a colored composition or a colored composition that exhibits a change in its absorption spectrum upon interacting with another substance, for example, upon binding to a biological compound or metal ion, upon reaction with another molecule or upon metabolism by an enzyme. In some aspects, colorimetric labels result in a detectable precipitate.

"Gene" means a chromosomal fragment that expresses a specific protein, including regulatory sequences preceding (5' non-coding sequences) and following (3' non-coding sequences) the coding sequence. The term gene includes endogenous genes in their natural location in the genome or foreign genes that are not normally found in the host organism, but are introduced into the host organism by recombinant molecular biology techniques.

"Mutagens" are agents that cause an increase in the rate of deletion or gene recombination. Mutagens may have genotoxic effect by damaging or otherwise interfering with the action of genes.

"Mutation" is a detectable and heritable structural change in the genetic material of an organism, and may include the addition or deletion of a whole chromosome, a structural change to a chromosomes (e.g., a translocation) and a structural change to a portion of the genomic sequence (e.g., point mutations, mutations to multiple sequential nucleotides and deletions of portions of the genomic sequence).

"DEL selection marker" means a disrupted genetic locus wherein: (1) the disruption comprises an insertion of a heterologous polynucleotide within the genetic locus; (2) said heterologous polynucleotide comprises one duplication of a portion of the genetic locus; (3) the head-to-tail (i.e., 5' end to 3' end) orientation of the duplicated portion of said heterologous polynucleotide is the same as that of the genetic locus; and (4) the genetic locus is useful for phenotypic selection of the cell when grown on suitable selection media. Various embodiments of DEL selection markers are described below.

"Selection medium" means a composition which can be used for phenotypic selection of cells. For example, a nutrient composition which lacks histidine can be used to selectively screen for yeast cells that are able to produce histidine. A nutrient composition which contains the antibiotic G418 can be used to selectively screen for cells that have the neo resistance gene. Other commonly used selection medium will be readily apparent to one of skill in the art.

"Suitable selection medium" refers to a selection medium having a composition that can be used for phenotypic selection of cells based upon the selection marker. Typically such a medium will comprise a composition that results in positive or negative selection of an appropriate cell types.

As stated above, it has been generally accepted that the carcinogenic potential of a chemical agent can, at least in part, be predicted by its mutagenicity (Grossblatt, N., 1983). This has enabled industries such as the chemical, cosmetic, food additive and pharmaceutical industries to alleviate the carcinogenic risk of their products by minimizing their mutagenic properties.

The DEL assay, also known as the intrachromosomal recombination assay, first described by Schiestl et al. (1988) using *Saccharomyces cerevisiae*, measures deletions of parts of the genomic sequence that are induced in target gene sequences by mutagens. Hence, this assay enables the evaluation of test compounds for their mutagenic potential.

Schiestl et al. (1988) reported a positive selection system for intrachromosomal recombination in the yeast, *Saccharomyces cerevisiae*, by integration of a plasmid containing an internal fragment of the HIS3 gene at the HIS3 locus resulting in two copies of the gene with terminal deletions at the 3' end of one and 5' end of the other.

The target gene sequences used in the DEL assay are genes whose function has been disrupted by the integration of an exogenous DNA fragment. For example, Schiestl et al. (1988) describes the use of a strain of *S. cerevisiae* designated "RSY6" (available from the ATCC, deposit number 201682), in which the HIS3 gene is disrupted by the integration of an exogenous DNA fragment. The resulting his-yeast strain requires histidine in its growth medium in order to grow. In histidine-free medium, a very small number of cells will spontaneously revert to his$^+$. However, when the cells are treated with a mutagen, the reversion rate increases beyond the normal background level.

In some instances a mutagen causes the formation of double-stranded DNA breaks. When such breaks occur in the disrupted gene, a cell's own repair mechanism may result in removal of the exogenous DNA and repair of the sequence (e.g., by single-strand annealing), thus the assays of the disclosure select for a deletion by recombination between a repeated sequence and reversion of the gene to its wild-type form.

The DEL assay has certain advantages over other mutagenicity assays. For example, it has been reported that the DEL assay has better predictability of carcinogenicity than the more commonly used *Salmonella* reverse mutation Ames assay. Many carcinogenic compounds which give negative results using the Ames assay are positive by the DEL method (Bishop and Schiestl, 2000).

However, one disadvantage of the currently available DEL assay is its impracticality for large scale and automated screening of potential mutagens (i.e., high throughput screening). For example, the current assay requires that cells be given enough time to grow into visible colonies in order to determine whether a test compound is a potential carcinogen. Moreover, because of the need to visualize growing colonies, the current assay cannot be miniaturized, for example, into a multi-well plate system, which would enable a reduction in the amount of test agent necessary. The disclosure overcomes this problem through the design of a liquid version of the DEL assay.

In one embodiment of the disclosure yeast growth can be identified in a non-clonogenic quantitative colorimetric assay, which measures the ability of proliferating cells to reduce MTT (3-4,5-dimethylthiazol-2-yl)-2,5-diphenyl tetrazolium bromide), a yellow tetrazolium salt, into a purple formazan precipitate. This reaction however, requires quenching and solubilizing the cells in order to measure the formazan precipitate.

MTT [3-(4,5-dimethylthiazol-2-yl)-2,5-diphenyltetrazolium bromide] assay, first described by Mosmann in 1983, is based on the ability of a mitochondrial dehydrogenase enzyme from viable cells to cleave the tetrazolium rings of the pale yellow MTT and form a dark blue formazan crystals which is largely impermeable to cell membranes, thus resulting in its accumulation within healthy cells. Solubilization of the cells by the addition of a detergent results in the liberation of the crystals which are solubilized. The number of surviving cells is directly proportional to the level of the formazan product created. The color can then be quantified using a simple colorimetric assay. The results can be read on a multiwell scanning spectrophotometer (ELISA reader).

An improvement upon the MTT assay can be made by substitution with the MTS tetrazolium compound [3-(4,5-dimethylthiazol-2-yl)-5-(3-carboxymethoxyphenyl)-2-(4-sulfophenyl)]-2H-tetrazolium, inner salt and an electron-coupling reagent PES (phenazine ethosulfate). The MTS compound is reduced by cells into a colored formazan product soluble in tissue culture medium. This reaction need not be quenched and cell proliferation can be directly measured by recording absorbance at 490 nm. Cell proliferation is proportional to the quantity of formazan product. Thus, the MTS assay is suitable as a colorimetric assay that can be used for high-throughput applications. Here MTS is used to construct a liquid based version of the yeast DEL assay capable of scoring DNA deletions on both 96 and 384-well plate formats.

The MTS tetrazolium compound is reduced to a colored formazan product in metabolically active cells; it is therefore an assay of viable cell number. A decline in values implies cell killing.

The disclosure provides a method and system for determining the mutagenic properties of an agent. In one embodiment, a recombinant cell comprising a DEL selectable marker is contacted with an agent suspected of being mutagenic under conditions wherein the agent and the cell interact. The viability of the cells are then measured in a selectable medium. The cells are assayed for viability using a colorgenic MTT or MTS assay or other mitochondrial cell viability assay. A mutagenic agent will provide improved recombination and survival in a selectable medium. For example, following contacting a cell with a test agent the cell's viability can be measured by adding an MTS solution to wells and incubating the cells with the MTS solution during which a colored formazan product is generated in viable cells. One advantage of the MTS assay is that the formazan product is soluble in tissue culture medium which avoids the solubilization step of the MTT assay. Viable cell number is then measured by reading absorbance at 490 nm in a Dynex microtitre plate reader. Cell viability is represented as the ratio of absorbance at time "x" (post drug addition) minus "blank" readings (medium with drug without cells) over absorbance at time zero (prior to drug addition) minus blank readings (medium without drug or cells), expressed as a percentage. 100% reflects viable cell numbers at the start of the experiment; values greater than 100% reflect cell proliferation and values less than 100% reflect cell disappearance (cytotoxicity). These interpretations can be made since values are expressed as a percentage of values at time zero and not relative to control cell populations which will have proliferated in the interim (and therefore increased in cell number). In one embodiment, the mutagenicity is directly proportional to the amount of DEL increase. For example, DEL is a ratio: growth of yeast on the selective medium (−HIS) compared to growth on complete medium. Also, one of the benefits of the DEL assay of the disclosure is that you can measure two endpoints with one assay; one can measure cytotoxicity (e.g, the amount of cell killing an agent causes a cell) and genotoxicity (the amount of mutagenesis an agent causes a cell). By this disclosure, one may expeditiously and economically test agents of unknown carcinogenic potential for DEL recombination in a manner that was previously unavailable.

The disclosure involves the use of cells having, as a component, a disrupted DEL-type selection marker. The marker is used to select those cells that undergo recombination events induced by a test mutagen. For example, if the test mutagen is mutagenic or carcinogenic, the rate of deletion or gene recombination will be increased relative to a control conferring to the cell increased survival in a selection medium. The viability of the cells is measured using a colorimetric assay comprising mitochondrial enzymatic activity (e.g., MTS or MTT assay). The disclosure demonstrates increased sensitivity relative to prior DEL assays. The methods of the disclosure enable detection of individual cell revertants or microcolonies of those cells very soon after treatment with test agents rather than after long term growth to identify growth colonies. This would obviate the need for allowing cells to grow into large colonies in order to allow detection.

In contrast to the currently available DEL assay, the methods and cells of the disclosure which are based on colorimetric detection (e.g., MTT or MTS reduction) of revertant cells on selection medium which allows for multi-well high throughput screening techniques for testing agents. The methods and cells of the disclosure enable a significant reduction in the amount of test agent necessary for mutagenicity testing. This can be a significant advantage where test agents are only available in small quantities. In addition, the use of MTT and MTS reduction allows the use of plate reader devices which can measure absorbance of the colorimetric signal.

In yet another embodiment, a colorimetric assay includes measuring beta galactosidase activity. This embodiment, utilizes a disrupted gene that undergoes recombination in the presence of a mutagenic compound or event (X-ray, gamma ray, etc). In one embodiment, a LacZ gene is fused to a galactose promoter and inserted into the genomic His3 locus in a eukaryotic cell such as *Saccharomyces cerevisiae* and disrupted by a plasmid with an internal fragment of the Gal-LacZ construct. The result is two copies of the Gal-LacZ construct with terminal deletions with a disruption by, for example, a URA3 gene (for selection) that revert to a functional Gal-LacZ phenotype upon exposure to genotoxic compounds and events.

In this embodiment, detection of the functional Gal-LacZ phenotype will be made possible with the addition of bromo-chloro-indolyl-galactopyranoside (X-gal) substrate to the media and a brief incubation period in the dark. Results will be read as the proportion of colonies turning blue (indicating genotoxicity/carcinogenicity) in the presence of the compound to the spontaneous reversions. In an HTS adaptation a spectrophotometer will be used to indicate differences in absorbencies.

As those with skill in the art will appreciate based upon the disclosure, any suitable eukaryotic cells may be used in the practice of this disclosure. For example, the cells may originate from vertebrate organisms, such as mammals, birds, fishes, reptiles and amphibians as well as invertebrates (e.g., insects, nematodes) and single-celled eukaryotes. For multi-celled eukaryotes, the cells may be derived from any organ or tissue, including blood, endothelium, thymus, spleen, bone marrow, liver, kidney, heart, testis, ovary, heart and skeletal muscle, and can be primary cells or cells derived from immortalized cell lines. Typical cells include human lymphoblastoid cell lines such as GM6804 (see, for example, Monnat, R. J. et al. (1992) and Aubrecht, J. et al. (1995)) and yeast cells, for example, of the species, *Saccharomyces cerevisiae*. Cells and cell lines for use in the methods of this disclosure may be obtained, for example, from the ATCC, Manassas, Va. 20110-2209.

As defined above, a DEL selection marker means a disrupted genetic locus wherein: (1) the disruption comprises an insertion of a polynucleotide within the genetic locus; (2) said polynucleotide comprises one duplication of a portion of the genetic locus; (3) the head-to-tail (i.e., 5' end to 3' end) orientation of the duplicated portion of said polynucleotide is the same as that of the genetic locus; and (4) the genetic locus is useful for phenotypic selection of the cell. For example, where a genetic locus comprises the elements A-B-C-D-E-F-G, suitable DEL selection markers based upon such a genetic locus can encompass the sequences A-B-C-B-C-D-E-F-G.

It will be appreciated by those with skill in the art, based upon the disclosure, that any suitable phenotype selection marker may be used for the DEL selection marker in the practice of the disclosure. It will be further appreciated that the type of selection marker used may, in part, depend upon the types of cells used in the practice of the disclosure.

In one embodiment of the disclosure, the DEL selection marker comprises a disruption of the function of a nutrient marker gene, such that the cell requires, as a result of this disruption, a specific nutrient in order to maintain its viability, metabolic activity or growth. In this embodiment, agents may be tested for their ability to cause reversion of the nutrient marker to its non-disrupted form, thus enabling cells to thrive in media lacking the corresponding nutrient. An exemplary nutrient marker includes the his3 in yeast cells which alters cellular requirements for histidine. Other nutrient markers will be apparent to those with skill in the art based upon the present disclosure.

In another embodiment, the DEL selection marker is a gene that conveys resistance to specific physical or chemical agents that would otherwise be toxic to the cell (i.e., hinder viability, metabolic activity or growth). Such "resistance markers" confer resistance to the cell against chemical agents, including, for example, antibiotics, antimetabolites or herbicides. A disruption of the function of the resistance marker gene causes toxicity to the cell when exposed to the toxic agent. As such, this embodiment comprises the testing of agents for their ability to cause reversion of the gene to its non-disrupted form, thereby enabling the cells to thrive in media containing the toxic substance. Exemplary resistance markers include dhfr (dihydrofolate reductase) which confers resistance to methotrexate; neo, which confers resistance to the aminoglycosides, neomycin and G418; and als and pat, which confer resistance to chlorsulfuron and phosphinotricin acetyltransferase, respectively (see, Wigler, M. et al. (1980); Colbere-Garapin, F. et al. (1981)). Other resistance markers are known to those with skill in the art or will be apparent to them based upon the present disclosure. Transfection or transformation of a cell with a disrupted resistance marker can be performed using techniques known to those of skill in the art.

It will also be appreciated that the selectable marker can be an enzyme the produces an enzyme that can convert a substrate to a detectable substrate (e.g., a colorimetric precipitate). For example, a selectable marker comprising an enzyme that converts a substrate to a colored precipitate can be disrupted by a polynucleotide, wherein an agent that modifies the DNA can be detected by a reversal of the disruption and production of a colored precipitate in the presence of a substrate for the enzyme. An example of such a colorimetric enzyme is beta-galactosidase encoded by the LacZ gene.

Those with skill in the art will appreciate, based upon this disclosure that, within the scope of the disclosure, DEL selection markers may also encompass a non-disrupted nutrient or resistance marker that is controllable by a secondary genetic element, wherein the function of the secondary genetic element is disrupted. Such secondary genetic element may include a gene which encodes a transcriptional activator protein which binds to an activation domain, thereby initiating or accelerating the rate of transcription of the nutrient or resistance marker. Hence, according to this embodiment, agents may be tested for their ability to cause reversion of the secondary genetic element to its functional form, thereby enabling the expression of the nutrient marker or resistance marker gene. An exemplary transcriptional activators and activation domain sequence combination includes the Tet-controlled transactivator which is part of the BD™ Tet-Off Gene Expression System (BD Biosciences, Palo Alto, Calif.). Other transcriptional activators and activation domain sequences are known to those with skill in the art or will apparent to them based upon this disclosure.

As will be further appreciated by those with skill in the art based upon the disclosure, the DEL selection markers may also encompass a non-disrupted negative selectivity marker gene that is controllable by a transcriptional repressor genetic element, wherein the function of the transcriptional repressor is disrupted. When active, the negative selectivity marker is toxic to the cell. Hence, according to such embodiments, agents may be tested for their ability to cause reversion of the transcriptional repressor to its functional form, thereby enabling the expression of the negative selectivity marker gene. An exemplary negative selectivity marker is the herpes simplex virus gene, thymidine kinase, which causes cytotoxicity in the presence of the drug, gancyclovir (Moolton (1986)). Other negative selectivity markers include Hprt (cytotoxicity in the presence of 6-thioguanine or 6-thioxanthine), and diphtheria toxin, ricin toxin, and cytosine deaminase (cytotoxicity in the presence of 5-fluorocytosine).

A transcriptional repressor genetic element would, when expressed, repress expression of the negative selectivity marker. An exemplary transcriptional repressor is through the use of RNA interference (RNAi) using methods, for example, described in Fire et al. (1998), in Brummelkamp et al. (2002) and by other methods known to those with skill in the art.

As will be apparent to those with skill in the art based upon the disclosure, the disrupted gene or genetic element that makes up a DEL selection marker used in the methods and cells of this disclosure, may be an endogenous gene or genetic element or it may be an exogenous gene or genetic element introduced into a progenitor cell by recombinant methods that are well known to those with skill in the art based upon the disclosure. Moreover, the cells used in this disclosure may be either haploid, having one copy of each type of chromosome, or diploid, having two copies of each chromosome-type. Hence, when diploid cells are used in the methods and cells of this disclosure and the disrupted gene or genetic element that makes up a DEL selection marker is an endogenous gene or genetic element, or when there is otherwise more than one copy of an endogenously existing gene or genetic element, typically all copies of the gene or genetic element will be disrupted for the practice of methods and use of cells of the disclosure.

In one embodiment, the DEL selection marker for use in *Saccharomyces cerevisiae* yeast cells comprises a HIS3 gene which is disrupted by insertion of the plasmid pRS6 as described in Schiestl et al. (1988) and which is contained in the *S. cerevisiae* strains RSY6 and RS112 as described in U.S. Pat. No. 4,997,757, (all of which are incorporated herein by reference in their entirety.

The disclosure uses a colorogenic/colorimetric detectable signal based on mitochondrial enzymes to detect cell viability. A number of other enzymatic colorimetric assays can be used in the methods of the disclosure. In another embodiment, a combination of detectable signals can be used. For example, a combination of bioluminescence and colorimetric methods can be used. It will be appreciated by those with skill in the art, based upon the disclosure, that any suitable bioluminescent marker may be used in the practice of the disclosure. It will be further appreciated that the type of bioluminescent marker used may, in part, depend upon the types of cells used in the practice of the disclosure. An exemplary bioluminescent marker for use in yeast cells is the firefly luciferase (luc) gene (GeneBank accession number AAA89084) driven by a constitutive glyceraldehydes-3-phosphate dehydrogenase (GPD) promoter. The bioluminescence catalyzed by the luc gene requires the substrate (luciferin) and energy in the form of endogenous ATP. So long as the medium in which the cells grow contains luciferin as a supplement, the bioluminescence of yeast cells is exclusively dependent on the availability of intracellular ATP. Since the intracellular ATP concentration is dependent on energy metabolism, the bioluminescent output represents the level of metabolic activities of yeast cell. In the methods of the disclosure, a test compound which causes a deletion recombination event to restore function of a DEL selection marker allows the cells to maintain metabolic activities and multiply in the absence of the applicable nutrient or the presence of a potentially cytotoxic substance.

Other bioluminescent markers that may be used in the methods and cells of this disclosure are known to those with skill in the art or will be apparent to them based upon the present disclosure. For example, Bronstein et al. (1994) describe bioluminescent markers that may be used in this disclosure. For combination assays, the bioluminescent markers and DEL selection markers that are used in the methods and cells of the disclosure may be incorporated into a cell by inserting the polynucleotide encoding such markers into an appropriate vector. Such vectors may be designed so that they are stably incorporated into the chromosomal DNA of a cell or they may be designed to express the applicable marker without chromosomal integration.

Expression vectors containing the necessary elements for transcriptional and translational control of the inserted coding sequence in a cell may be used to incorporate into a cell a biologically active enzyme (for generation of a colorimetric signal), a bioluminescent marker or a DEL selection marker that will become biologically active upon reversion following treatment with a test agent. The transcriptional and translational control elements include regulatory sequences, such as enhancers, constitutive and inducible promoters, and 5' and 3' untranslated regions in the vector and in polynucleotide sequences encoding the applicable marker. Such elements may vary in their strength and specificity. Specific initiation signals may also be used to achieve more efficient translation of sequences encoding the markers. Such signals include the ATG initiation codon and adjacent sequences, e.g. the Kozak sequence. In cases where sequences encoding a marker and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used. (See, e.g., Scharf, D. et al. (1994)).

Methods which are well known to those skilled in the art based upon the disclosure may be used to construct expression vectors containing polynucleotides encoding colorimetric enzymes, bioluminescent markers or DEL selection markers and appropriate transcriptional and translational control elements.

For embodiments of the disclosure in which the DEL selection marker involves disruption of an endogenous gene, a typical method of incorporating a DEL selection marker is through homologous recombination. Homologous recombination methods for incorporating engineered gene constructs into the chromosomal DNA of cells are well known to those skilled in the art and/or those that will be further apparent to them based upon the disclosure.

In the preparation of cells containing a DEL selection marker, a DEL selection marker targeting vector is introduced into a cell having the undisrupted target gene. The introduced vector targets the gene using a nucleotide sequence in the vector that is homologous to the target gene. The homologous sequence facilitates hybridization between the vector and the sequence of the target gene. Hybridization causes integration of the vector sequence into the target gene through a crossover event, resulting in disruption of the target gene.

General principles regarding the construction of vectors used for targeting are reviewed in Bradley et al. (1992). Guidance regarding the selection and use of sequences effective for homologous recombination, based on the description, is described in the literature (see, for example, Deng and Capecchi (1992); Bollag et al. (1989); and Waldman and Liskay (1988)).

As those skilled in the art will recognize based upon the disclosure, a wide variety of cloning vectors may be used as vector backbones in the construction of the DEL selection marker targeting vectors of the disclosure, including pBluescript-related plasmids (e.g., Bluescript KS+11), pQE70, pQE60, pQE-9, pBS, pD10, phagescript, phiX174, pBK Phagemid, pNH8A, pNH16a, pNH18Z, pNH46A, ptrc99a, pKK223-3, pKK233-3, pDR540, and pRIT5 PWLNEO, pSV2CAT, pXT1, pSG (Stratagene), pSVK3, PBPV, PMSG, and pSVL, pBR322 and pBR322-based vectors, pMB9, pBR325, pKH47, pBR328, pHC79, phage Charon 28, pKB11, pKSV-10, pK19 related plasmids, pUC plasmids, and the pGEM series of plasmids. These vectors are available from a variety of commercial sources (e.g., Boehringer Mannheim Biochemicals, Indianapolis, Ind.; Qiagen, Valencia, Calif.; Stratagene, La Jolla, Calif.; Promega, Madison, Wis.; and New England Biolabs, Beverly, Mas.). However, any other vectors, e.g. plasmids, viruses, or parts thereof, may be used as long as they are replicable and viable in the desired host. The vector may also comprise sequences which enable it to replicate in a host cell whose genome is to be modified. The use of such a vector can expand the interaction period during which recombination can occur, increasing the efficiency of targeting (see Ausubel et al (2003), Unit 9.16, FIG. 9.16.1).

The specific host cell employed for propagating the targeting vectors of the disclosure is not critical. Examples include *E. coli* K12 RR1 (Bolivar et al., (1977)), *E. coli* K12 HB101 (ATCC No. 33694), *E. coli* MM21 (ATCC No. 336780), *E. coli* DH1 (ATCC No. 33849), *E. coli* strain DH5a, and *E. coli* STBL2. Alternatively, host cells such as *C. cerevisiae* or *B. subtilis* can be used. The above-mentioned exemplary hosts, as well as other suitable hosts are available commercially (e.g., Stratagene, La Jolla, Calif.; and Life Technologies, Rockville, Md.).

Typically, the targeting constructs for disruption of target gene also include an exogenous nucleotide sequence encoding a resistance marker protein. As described above regarding various possible types of DEL selection markers, a resistance marker conveys resistance to specific physical or chemical agents that would otherwise be toxic to a cell. The resistance marker gene is positioned between two flanking homology regions so that it integrates into the target gene following the crossover event in a manner such that the resistance marker gene is positioned for expression after integration. By imposing the selectable condition, one may isolate cells that stably express the resistance marker-encoding vector sequence from other cells that have not successfully integrated the vector sequence on the basis of viability.

The above-described use of a resistance marker does not distinguish between cells that have integrated the vector by targeted homologous recombination at the target gene locus rather than by random, non-homologous integration of vector sequence into any chromosomal position. Therefore, when using a replacement vector for homologous recombination to make the cells of the disclosure, it is also useful to include a polynucleotide encoding a negative selectivity marker protein. As described above regarding various possible types of DEL selection markers, negative selectivity marker is a protein that when expressed is toxic to a cell. The nucleotide sequence encoding a negative selectivity marker is positioned outside of the two homology regions of the replacement vector. Given this positioning, cells will only integrate and stably express a negative selectable marker if integration occurs by random, non-homologous recombination; homologous recombination between the target gene and the two regions of homology in the targeting construct excludes the sequence encoding the negative selectable marker from integration. Thus, by imposing the negative condition, cells that have integrated the targeting vector by random, non-homologous recombination lose viability.

Vectors containing a colorimetric enzyme maker and/or bioluminescent markers and a DEL selection marker (or target sequences thereof) may be introduced into a cell according to standard methods well known to those with skill in the art or those that will be apparent to them based upon the disclosure. As those skilled in the art will appreciate, the transformation protocol chosen will depend upon, for example, the cell type and the nature of the gene of interest, and can be chosen based upon routine experimentation. Several transformation protocols are reviewed in Kaufman (1988). Methods may include electroporation, calcium-phosphate precipitation, retroviral infection, microinjection, biolistics, liposome transfection, DEAE-dextran transfection, or transferrinfection (see, e.g., Neumann et al. (1982); Potter et al. (1984); Chu et al. (1987); Thomas and Capecchi (1987); Baum et al. (1994); Biewenga et al., (1997); Zhang et al., (1993); Ray and Gage (1992); Lo (1983); Nickoloff et al. (1998); Linney et al. (1999); Zimmer and Gruss, (1989); and Robertson et al., (1986). A typical method in the practice of the disclosure for introducing foreign DNA into a yeast cell involves the use of lithium acetate/PEG, as described in Gietz and Woods (2002).

Cells to be used in the practice of the methods of the disclosure may be stored and cultured according to methods well known to those with skill in the art based upon the present disclosure. For example, mammalian cells may be cultured according to methods described in Bonifacino et al. (2003), Chapter 1. Yeast cells may be cultured according to general methods described in Ausubel et al. (2003), Chapter 13.

In the practice of the methods of the disclosure, the treatment of cells with a test agent may be employed according to methods known by those with skill in the art based upon the disclosure. The method used will depend upon many variables, including the types of cells used, characteristics of the DEL selection marker and characteristics of the test agents used.

In one embodiment, yeast cells (*Saccharomyces cerevisiae*) having a disruption of the his gene as the DEL selection marker are treated with test agents in 25 ml tubes and then plated for about 48 h at 30° C. Following treatment the cells are washed, for example, with PBS, and sonicated to assure dissociation of the cells into a single-cell suspension. The cells are then plated at an appropriate dilution (see below) onto medium lacking histidine as well as standard medium containing histidine. The histidine-lacking medium is used to determine recombination frequency. Standard medium (medium containing histidine) is used to determine the overall toxicity of the test agent.

In order to determine the optimal cell dilution for plating, the cells may be counted using a cell counting device (e.g., using a Coulter Particle Counter, Coulter Corp., Miami, Fla.). Ten fold serial dilutions are then prepared ($D_0$-$D_5$, wherein $D_0$ is the initial cell culture). The optimal cell dilution is such that there are sufficient cells to be able to measure: (a) the toxicity of the test agent; (b) the baseline recombination frequency of the cells (without treatment); and (c) the level of DEL recombination following treatment. For example, a typical dilution when using S. cerevisiae cells is $1 \times 10^5$ to $1 \times 10^7$ cells per mL.

For high throughput detection, cells may be plated on multi-well plates (e.g., 12, 24 or 48, 96, or 384 wells). The cells are then incubated for a sufficient time to enable revertant colonies to grow, typically 96 or 384-well plates for about 17 hours at 30° C.

As those with skill in the art will appreciate, based upon the disclosure, revertant colonies are detected using an MTT or MTS assay. The MTT or MTS assay measures reduction of MTT or MTS by a mitochondrial enzyme. The mitochondrial enzyme will be present in viable cells thus providing an indication of living cells in the selection medium. Where a combination assay is used, the detection may be performed by measuring both the colorimetric signal produced by enzymes in the mitochondria in the presence of MTT or MTS as well as a bioluminescence assay. Bioluminescence may be visualized using any light detection device, for example, a LumiImager® F1 photon-counting device (Roche Diagnostics, Indianapolis, Ind.) that may be used to identify colonies in multi-well plates. Other light detection devices that may be used include NightOwl (Berthold, Germany) and Kodak IS1000 (Kodak, Rochester, Md.). Furthermore, the digital image of bioluminescent colonies of cells is suitable for automated data evaluation using image analysis software (for example, Image Plus PrO™, ver. 4.1 (Media Cybernetics, Inc., Carlsbad, Calif.).

The reversion frequency may be expressed as the number of revertant cells per the total number of cells that survive treatment with the test agent. For example, for S. cerevisiae having the his⁻ DEL selection marker the following formula may be used to calculate reversion frequency:

$FR=(R \times D)/(S \times D')$; where FR=reversion frequency; R=number of revertant colonies on histidine lacking medium; S=number of colonies on standard media; D=dilution factor of cells plated on histidine lacking media; and D'=dilution factor of cells plated on standard media.

Any statistically significant increase in the reversion frequency as compared to a control will be indicative of a test agent having potential genotoxic and/or carcinogenic properties. The determination of statistical significance is well known to those with skill in the art or will be apparent based upon the disclosure. A typical positive result will yield a p-value that is no more than 0.05, more typically no more than 0.01 (Brownlee (1960)).

As will be apparent to those with skill in the art based upon the disclosure, the determination in a cell population of reversion frequency as compared to a control requires correction for secondary effects of a test agent. For example, certain test agents that cause increased reversion frequency, may also reduce the rate of growth and/or division of cells. As a result, the number of revertant cells in untreated control cells may grow faster than those in the treated cell population such that the total population in the control exceeds those in the treated cells.

A method for correcting such secondary effects is by immobilizing populations of individual treated and control cells, e.g., using selection media which is solid or semi-solid, such that the cells form individual colonies. The reversion frequency would then be determined based upon the number of detectable colonies or micro-colonies.

The above-described assay methods are for illustrative purposes only. Those with skill in the art will appreciate based upon the disclosure that a variety of assay formats may be utilized in the practice of this disclosure. Variations may be made based upon the types of cells, DEL selection markers, colorimetric markers, the combination of colorimetric and bioluminescence markers and test agents used, methods of treating and culturing cells and methods of detection of revertants.

Although one described use of the methods and cells of the disclosure is for detection of chemical mutagenic/genotoxic agents, the disclosure is also applicable to other agents that may cause mutagenicity/genotoxicity, for example, environmental agents such as ionizing radiation.

The following Examples are to be construed as merely illustrative of the practice of the invention and not limitative of the remainder of the disclosure in any manner whatsoever.

EXAMPLES

DNA rearrangements including DNA deletions are involved in carcinogenesis. An assay screening for DNA deletions in yeast (DEL assay) can detect Salmonella/Ames assay negative as well as positive carcinogens. Among 58 compounds (mostly false negatives and false positives with the Salmonella assay), the DEL assay correctly identified the carcinogenic activity of 86% compared with 36% that were correctly identified in the Salmonella assay. In addition, carcinogens have also been reported to induce DNA deletions in related assays in vitro with human cells and in vivo with mice.

The RS112 yeast DEL assay tester strain of Saccharomyces cerevisiae contains a plasmid with an internal fragment of the HIS3 gene integrated at the genomic HIS3 locus, yielding an integrative disruption of the HIS3 gene. This disruption results in two copies of the HIS3 gene, each copy having one terminal deletion. Recombination between the two his3 deletion alleles results in reversion to HIS3⁺ and growth in the absence of histidine. This recombination event leads to a 6 kb DNA deletion comprising the integrated plasmid leading to deletion (DEL) events. The assay utilizing DEL events involves overnight growth of a single colony of the RS112 strain and subsequent subculture with the presence or absence of the chemical being tested for 17 hours at 30° C. under constant shaking. Yeast are then plated onto SC medium to determine the number of survivors (individual colonies are counted) and onto SC-HIS medium to score for DEL events. The traditional DEL assay is very powerful if one is testing a limited number of chemicals but becomes impractical for screening large numbers of chemicals and chemical libraries.

Yeast nitrogen base 0.67%, glucose 2%, agar 2% plus the following amino acids and bases per 600 ml of distilled water: 40 mg each of adenine sulphate, 1-isoleucine, 1-leucine, 1-lysine-HCl, 1-tyrosine, 30 mg of 1-arginine-HCl, 1-histidine-HCl, 1-methionine, uracil, 60 mg of 1-tryptohpan. For well-based experiments, agar was not added.

Yeast nitrogen base 0.67%, glucose 2%, plus the following amino acids and bases per 600 ml of distilled water were added after autoclaving: 12 mg uracil, 24 mg adenine sulphate, 12 mg 1-histidine.

The following compounds were purchased from Sigma: actinomycin D (CAS No. 50-76-0) dissolved in 0.2% acetone, ethyl methanesulfonate (CAS No. 62-50-0), camptothecin (CAS No. 7689-03-4), 4-nitroquinoline-1-oxide (CAS No. 56-57-5) dissolved in 0.2% DMSO, mitomycin C (CAS No. 50-07-0), CrCl3 (CAS No. 10025-73-7), K2Cr2O7 (CAS No. 1333-82-0), benzene (CAS No. 71-43-2), methylmethane sulfonate (CAS No. 66-27-3), cyclophosphamide monohydrate (CAS No. 6055-19-2), dimethyl sulfoxide (CAS No. 67-68-5) acetone (CAS No. 67-64-1). The following compounds were purchased from VWR: carmustine (CAS No. 154-93-8), chlorambucil (CAS No. 305-03-3) and cisplatin (CAS No. 15663-27-1). Stock solutions of each compound were prepared in water except for 4-nitroquinoline-1-oxide (0.4% acetone), camptothecin (DMSO), and chlorambucil (1:50 HCL-methanol). Acetone at about 0.1% (e.g., 0.05-2%), DMSO at about 1% (e.g., 0.1-2%) and HCL-methanol were tested for DEL induction since they were used as solvents.

The diploid S. cerevisiae strain RS112 was used to determine the frequency of DEL recombination: MATa/MATα ura3-52/ura3-52 leu2-3,112/leu2-Δ98 trp5-27/TRP5 arg4-3/ARG4 ade2-40/ade2-101 ilv1-92/ILV1 HIS3::pRS6/his3 Δ200 LYS2/lys2-801.

For 384-well plate format, 1 μl of yeast (~100,000 cells) was pipetted into 8 microplate wells for each compound, four of which containing 70 μl SC media and four containing 70 μl SC-HIS media; each well was supplemented with 14 μl of MTS and 5 μl of compound. For 96-well plate format, the above was consistent except media, MTS, and compound volumes were 100 μl, 20 μl, and 7 μl, respectively. Control wells were treated with water in lieu of compound. The outermost columns of the 96-well plate and outer two columns of each 384-well plate were excluded from experimentation lest edge evaporative effects alter the data. Plates were incubated at 30° C. at normal atmosphere during which yeast were grown in the presence of the tested compound and 490 nm absorbance was measured 10-18 hr later using a Molecular Devices SpectraMax M5 microplate reader (Sunnyvale, Calif.).

A mock experiment was setup to measure the sensitivity of the well-based DEL assay. On a 96 well plate, wells containing 100,000 RS112 yeast cells in 100 μl SC-HIS media were supplemented in six-plicate with 5 μl of RS112 His+ revertant cells ranging from 0 cells to 1000 cells. 20 μl MTS was added to each well, plates were incubated at 30° C., and 490 nm absorbance was read hourly between 12 and 24 hrs using a Molecular Devices SpectraMax M5 microplate reader (Sunnyvale, Calif.).

Survival for a given compound treatment was quantified by averaging the absorbance across the four treated wells in SC media and dividing that by the average absorbance of control wells. DEL induction was quantified by dividing the absorbance of each SC-HIS well by the corresponding paired SC well. Thus for each compound done in quadruplicate, each plate contains a set of 4 different measurements of DEL induction. For each compound, ratio of the average DEL induction in treated versus control cultures was taken as the fold-increase in DEL events (HIS+ growth). A Student's t-test was performed on the 4 measurements of DEL induction and the same measurements recorded from control wells to determine significance of the fold-increase. It should be noted that this value of fold-increase is analyzed statistically for significance and not absolute; thus two different chemicals may have the same fold-increase but varying levels of significance. In plots and tables, data from a single experiment performed in quadruplicate is presented; all experiments were repeated independently in at least 3 separate experiments in both 96 and 384-well plate formats.

The DEL assay has been modified to a well-based format. To determine experimental sensitivity a mock experiment was performed which simulated the DEL induction using 96-well plates. The assay was most sensitive when absorbance was measured 18 hours post incubation at which time as few as 25 RS112 His+ revertant cells (corresponding to 2.5 DEL events/10,000 cells) could be significantly differentiated from spontaneous background levels in 100,000 RS112 cells. 250 RS112 His+ revertant cells were significantly detected 12 hours after dispersement into microwells (FIG. 1) suggesting that strong inducers of DEL recombination which induce 25-250 or more DEL events/10,000 cells are rapidly discernable using the well-based DEL assay.

To validate the well-based DEL assay, nine carcinogens previously characterized by the plate-based DEL assay were used in both 96- and 384-well plate formats. In as little as 10-12H after the addition of MTS all of the high and moderate genotoxic treatments (comparable to >250 DEL events induced per 100,000 cells as observed by the plate-based assay) were readily distinguishable from controls. For most compounds tested, the concentration range was analogous to those ranges reported in previous studies with the plate-based DEL assay, yet for MMS the concentration range was decreased to avoid elevated cytotoxicity. For the concentrations used here, these compounds showed varied levels of induction of DEL recombination in yeast. In this way, the sensitivity of the well-based assay can be validated using data previously acquired using the plate-based assay. In addition, a group of crosslinking agents previously uncharacterized by the DEL assay were tested for genotoxicity induction.

Figure 2A:
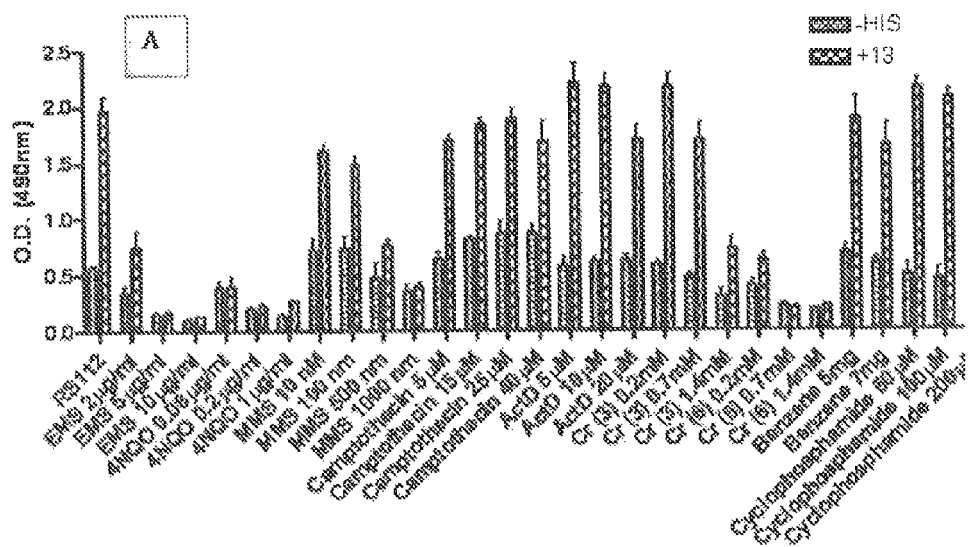
FIG. 2A-C show well-based DEL assay evaluating the cytotoxicity and genotoxicity of 13 carcinogens by measuring O.D. (490 nm) 14 h after the addition of MTS. Cytotoxicity in treated samples is represented by diminished growth in +13 media compared to untreated yeast labeled "RS112." Genotoxicity is represented by increased growth in –HIS media compared to untreated yeast. In panel A, compounds were previously tested using the DEL assay; panel B, crosslinking agents previously uncharacterized by DEL assay; panel C, crosslinking agents previously uncharacterized by DEL assay. Experiments performed in panels A, B, and C were respectively done on a single 384-well plate; 4 repeats for each treatment group were used and the results are presented as means±SD. The experiment was repeated at least three times in both 96 and 386-well plate formats each time yielding similar results.
Figure 2B:
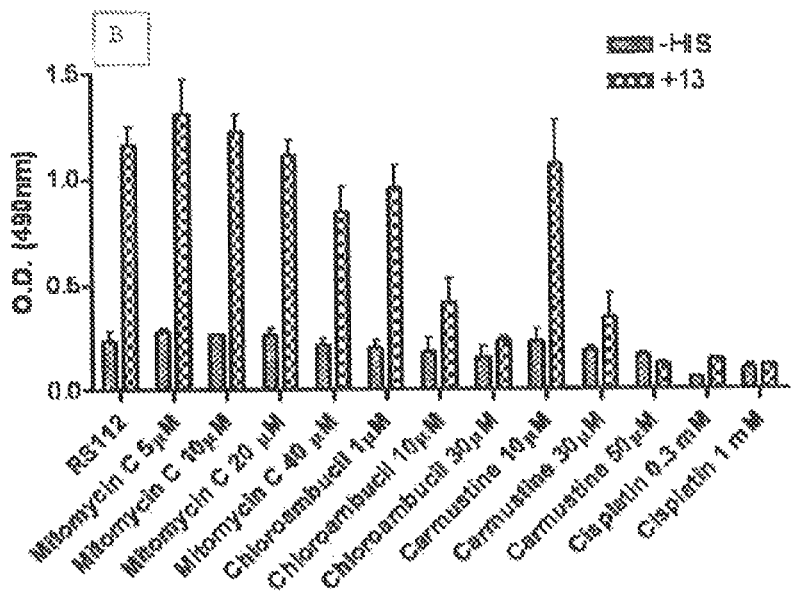
Figure 2C:
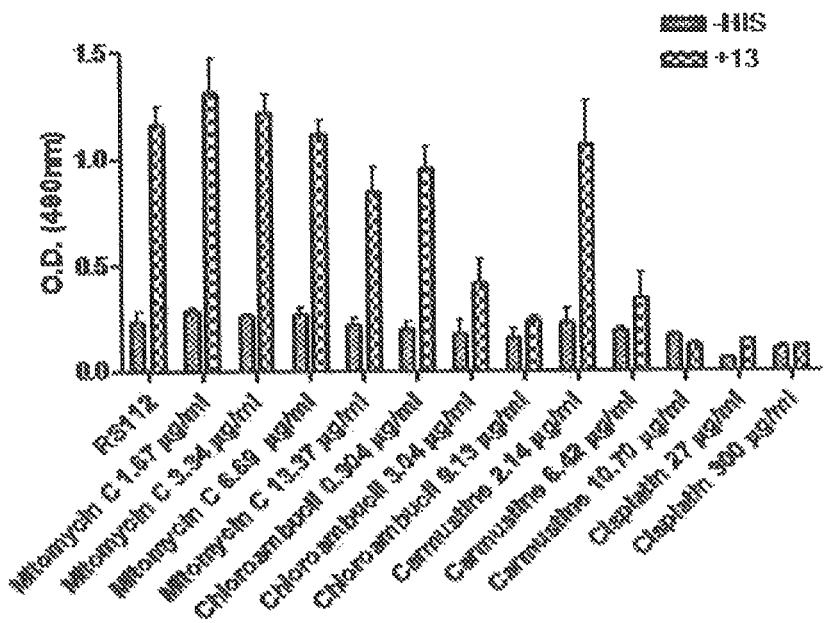

The growth measurement of 13 different carcinogens tested by the well-based DEL assay is plotted in FIG. 2, and the calculated cytotoxicity and genotoxicity are presented in Table 1. Yeast cells exposed to 2, 5 and 10 μg/ml EMS showed diminished growth in +13 media and increased growth in –HIS media. The toxic effect of EMS on survival is dose-related as greater survival was observed in samples treated with the 2 μg/ml EMS, while those treated with 10 μg/ml produced the lowest survival. Although for each EMS treatment, the DEL fold-increase was significantly greater than that observed in untreated controls, no quantitative genotoxicity relationship with dose was discernable as with the plate-based assay.

| Compound | DEL (fold increase)[1] | DEL significance[2] | Cytotoxicity (% survival)[3] | Cytotoxicity significance |
|---|---|---|---|---|
| EMS[4] (2 μg/ml) | 1.59 | *** | 38.2 | *** |
| EMS (5 μg/ml) | 3.19 | *** | 8.36 | *** |
| EMS (10 μg/ml) | 2.65 | *** | 6.70 | *** |
| 4NQO[4] (0.08 μg/ml) | 3.39 | *** | 20.3 | *** |
| 4NQO (0.2 μg/ml) | 3.05 | *** | 11.7 | *** |
| 4NQO (1 μg/ml) | 1.78 | *** | 13.5 | *** |
| MMS[4] (10 nM) | 1.54 | ** | 81.2 | *** |
| MMS (100 nM) | 1.68 | *** | 74.8 | *** |
| MMS (500 nM) | 2.16 | *** | 38.6 | *** |
| MMS (1000 nM) | 3.09 | *** | 20.3 | *** |
| Camptothecin (5 μM) | 1.28 | ** | 86.1 | *** |

-continued

| Compound | DEL (fold increase)[1] | DEL significance[2] | Cytotoxicity (% survival)[3] | Cytotoxicity significance |
|---|---|---|---|---|
| Camptothecin (15 µM) | 1.53 | *** | 93.1 | * |
| Camptothecin (25 µM) | 1.57 | *** | 95.7 | * |
| Camptothecin (40 µM) | 1.77 | *** | 85.6 | *** |
| ActD[4] (5 µM) | 0.89 | ns | 112.0 | na |
| ActD (10 µM) | 0.96 | ns | 110.2 | na |
| ActD (20 µM) | 1.26 | ** | 86.3 | ** |
| Cr (3) (0.2 mM) | 0.93 | ns | 110.1 | na |
| Cr (3) (0.7 mM) | 0.98 | ns | 85.8 | ** |
| Cr (3) (1.4 mM) | 1.44 | *** | 36.8 | *** |
| Cr (6) (0.2 mM) | 2.13 | *** | 32.1 | *** |
| Cr (6) (0.7 mM) | 3.78 | *** | 9.91 | *** |
| Cr (6) (1.4 mM) | 3.12 | *** | 10.8 | *** |
| Benzene (0.25 mg/ml) | 1.77 | *** | 96.0 | ns |
| Benzene (0.40 mg/ml) | 2.31 | *** | 83.7 | ** |
| Cyclophosphamide (50 µM) | 0.77 | ns | 109.4 | na |
| Cyclophosphamide (100 µM) | 0.74 | ns | 104.5 | na |
| Cyclophosphamide (200 µM) | 0.95 | ns | 96.2 | ns |
| Mitomycin C 5 µM | 1.07 | ns | 112.7 | na |
| Mitomycin C 10 µM | 1.07 | ns | 105.1 | na |
| Mitomycin C 20 µM | 1.19 | * | 95.7 | ns |
| Mitomycin C 40 µM | 1.29 | ** | 72.5 | *** |
| Chlorambucil 1 µM | 1.18 | * | 82.4 | ** |
| Chlorambucil 10 µM | 2.37 | *** | 35.7 | *** |
| Chlorambucil 30 µM | 3.58 | *** | 20.5 | *** |
| Carmustine 10 µM | 1.18 | * | 91.8 | * |
| Carmustine 30 µM | 3.35 | *** | 29.5 | *** |
| Carmustine 50 µM | 7.63 | *** | 10.7 | *** |
| Cisplatin 0.3 mM | 1.92 | *** | 12.4 | *** |
| Cisplatin 1 mM | 4.57 | *** | 9.9 | *** |
| DMSO 1% | 0.96 | ns | | |
| Acetone 0.4% | 0.96 | ns | | |
| HCL-methanol (1:50) 0.5% | 0.95 | ns | | |

[1]Fold DEL increase was calculated by dividing the DEL induction measured for the respective compound concentration by that of the controls performed on the same plate. The concentration listed is the final concentration treated in each well. Each experiment was repeated at least 3 times on separate plates and similar results were attained in each measurement.
[2]Significance * ($p < 0.05$),  ($p < 0.01$), * ($p < 0.005$). ns—not significant ($p > 0.05$).
[3]Cytoxicity was calculated by averaging the absorbance across the four treated wells in SC media and dividing that by the average absorbance of control wells.
[4]Abbreviations: EMS: ethyl methanesulfonate; 4NQO: 4-nitroquinoline-1-oxide; MMS: methylmethane sulfonate; ActD: actinomycin D 4-nitroquinoline-1-oxide (4NQO) induced a significant DEL fold-increase (growth in –HIS medium) even at concentrations as low as 0.08 µg/ml (Table 1) and all concentrations tested between 0.08 and 1.0 µg/ml were cytotoxic as measured by growth in +13 media (FIG. 2). Camptothecin induced significant genotoxicity at each concentration 5-40 µM (1.7-13.9 µg/ml) indicated by increased growth in –HIS media, and various degrees of cytotoxicity were observed at each of the concentrations tested. Solvents DMSO and acetone, used to dissolve camptothecin and 4NQO, respectively, were scored for DNA deletion potential; neither solvents generated any differentiable response from control treated yeast. Methylmethane sulfonate caused a significant increase in DEL fold-increase even at the lowest dose tested of 10 nM (0.0011 µg/ml) and was increasingly significantly cytotoxic at each concentration between 10-1000 nM. 20 µM (~0.11 µg/ml) actinomycin D also caused a significant DEL fold-increase as well as slight cytotoxicity.

Both chromium III ($CrCl_3$) and chromium VI ($K_2Cr_2O_7$) induced DNA deletions in previous experiments and were also tested for DEL induction in well-based format (Table 1 and FIG. 2a). Chromium III did not induce any genotoxic events at concentrations of 0.2 (~32 µg/ml) or 0.7 mM (~111 µg/ml), yet a significant increase in DEL recombination was observed at 1.4 mM (~222 µg/ml). Chromium VI showed a very potent induction of the DEL assay and severely decreased survival with increased dose between 0.2 and 1.4 mM (~20-140 µg/ml). At benzene concentrations 0.25 and 0.40 mg/ml (~250 and 400 µg/ml, respectively) significant DEL induction was observed; no DEL fold-increase was observed with cyclophosphamide up to 200 µM.

The chemotherapeutic agent mitomycin C, a cross linking agent previously uncharacterized by the yeast DEL assay, caused significant increases in genotoxicity ($HIS^+$ growth) in yeast at concentrations of 20 µM (~6.7 µg/ml) and above whereas cytotoxicity was only significantly observed at 40 µM (FIG. 2b and Table 1). Chlorambucil, also a drug used for chemotherapy, caused significant genotoxicity and cytotoxicity at concentrations as low as 1 µM (~0.3 µg/ml), while carmustine caused more pronounced genotoxic and cytotoxic effects at concentrations above 30 µM (~2.1 µg/ml). HCL-methanol, used as a solvent for chlorambucil, by itself induced no DEL events compared to control treated yeast. Cisplatin, another widely used chemotherapeutic agent, caused significant cytotoxicity and genotoxicity at concentrations 0.3 and 1 mM (~27 and 300 µg/ml, respectively).

The disclosure provides a method and system for rapid determination of DEL recombination effects. It has been micro-scaled to 96 or 384-well format using the colorimetric agent MTS. To validate the assay compounds thoroughly studied with the traditional agar plate-based DEL assay were used. Strong and medium genotoxic compounds are readily distinguished with the well-based assay. In as little as 10-12 h after the addition of MTS all of the high and moderate genotoxic treatments (comparable to >25 DEL events induced per 10,000 cells as quantified by the plate based assay) were readily distinguishable from controls. Data herein is reported from experiments done with 384-well plates, yet the same measurements were also done on 96-well plates giving comparable results.

A comparison can be made between the sensitivity of the well-based DEL assay and the traditional plate based assay. With chromium III, the lowest dose which induced significant genotoxicity with the traditional agar plate version was 0.7 mM (~111 µg/ml) whereas in well-based format the lowest detectable concentration was 1.4 mM (~222 µg/ml). With the plate-based assay it was previously observed that 1.4 mM (~222 µg/ml) Cr (III) corresponded to 33.6 DEL events per 100,000 cells. If one considers that the background as tested in the present study is about 20 DEL events per 100,000 cells, this is a very small increase of approximately 13.6 cells above background. The fact that this toxicity level was significantly detectable here (Table 1) corresponds well with the mock experiment done to identify the sensitivity of well-based DEL assay (FIG. 1) in which the sensitivity was found to be somewhere between 12.5-25.0 DEL events per 100,000 cells. The well-based assay is suited for rapidly assessing genotoxicity of many treatments simultaneously.

After validating the well-based DEL assay with carcinogens previously characterized by the plate-based assay, the well-based DEL assay was used to evaluate the DEL potential of four previously uncharacterized carcinogens. Carmustine, chlorambucil, cisplatin, and mitomycin C are effective producers of DNA-DNA interstrand crosslinks and are frequently used as chemotherapeutic agents. Treatment with each of these crosslinking agents induced a significant increase in DEL events using the well-based DEL assay (FIG. 2b). This indicates that crosslinking agents can produce DNA deletion events in yeast, and that the DEL assay is capable of detecting carcinogens whose main mechanism of carcinogenesis is through DNA crosslink production.

The well-based assay is economically superior to the plate-based assay and substantially less labor intensive. To perform the plate-based assay, four to five days are needed to perform the entire assay and score colonies. In the well-based assay, significant results can be collected in as few as 10-12 hours, and moreover there is no requirement to count and score colonies. The well-based assay is intended as an easy method to determine the binary presence or lack of genotoxicity.

In some tests exposing yeast to extremely high cytotoxic treatments of nongenotoxic compounds can yield a false-positive report of genotoxicity. Such high cytoxic treatments can cause so much yeast killing that the absorbance measured in both +13 and –HIS wells is reduced near to background levels; thus when the ratio of growth in –HIS to +13 is taken, it nears unity.

The well-based version of the DEL assay is amenable to multiple formats. For example, yeast could be treated in 5 ml liquid cultures for 17 hours (as done for the plate-based assay) and then afterward scored in +13 and –HIS liquid media using MTS. When this format was used, a similar qualification of genotoxicity was measured for each of the compounds. The well-based assay is also adaptable for high-throughput screening. Generally high-throughput screens use one compound per well. Also, the toxicity of many compounds is only discernable within a specific dosage range. Thus if a high-throughput screen is preformed at a single concentration for each compound, the genotoxicity of some compounds may be overlooked. Accordingly, multiple concentrations and/or repeat measurements can be performed in one well-based assay.

The DEL assay was micro-scaled for use in a 96 or 384-well format, adept for high-throughput screen-based assays. This format is sensitive enough to detect at least 2.5 DEL events per 10,000 cells and was used to assess the genotoxicity of 13 different compounds tested at various concentrations. Crosslinking agents previously uncharacterized with the DEL assay were strong inducers of DNA deletions using this assay. The well-based DEL assay described here is ergonomically superior and can report genotoxicity much more rapidly than the traditional plate-based assay. The well-based DEL assay is well suited for rapidly qualifying the genotoxicity of a large number of compounds and is amenable to automation in its current format for high-throughput purposes.

By changing the selection scheme, the assay can be used to detect aneugenic activity. For example, the effects induced by aneugenic agents on chromosome segregation are manifold. Because the assays of the disclosure measure the deletion or recombination of segments of DNA conferring survival to a cell, measuring DNA loss of a cellular toxin can be detected.

Another system comprises a DEL-LacZ Assay. The construct useful for this embodiment is developed by insertion of lacZ into His3 gene of a yeast expression vector. Strategene pESC-His vector is used as a starting material. The His3 gene contains two HindIII sites that were used to insert the lacZ gene. Cloning of lacZ into pESC-His was performed by designing lacZ primers containing HindIII cut sites on each of the forward and reverse primers. pEN24 is a plasmid containing the lacZ gene that was used as a PCR template to isolate the lacZ gene for cloning into pESC-His. Upon completion of this step, the lacZ gene is in correct orientation within the His3 locus on the plasmid pHis-Lac, flanked by approximately 500 bp homology sequences.

pHis-Lac was transformed into strain Y433. Disruption of lacZ gene by Ura3—Insert Ura3 (promoter+CDS) into EcoRV site within the His3 gene. This yields ~1800 bp sequence homology for the disrupted lacZ gene on either side of the Ura3 gene. Promoters for both the lacZ and Ura3 genes were included in order to avoid formation of a single fusion protein once integrated into the yeast genome.

Insertion of the LacZ gene into the His3 HindIII sites and the insertion of the Ura3 gene provides a construct with the polynucleotide sequence shown in SEQ ID NO:1.

A number of embodiments have been described. Nevertheless, it will be understood that various modifications may be made without departing from the spirit and scope of the description. Accordingly, other embodiments are within the scope of the following claims.

What is claimed is:

1. A method for characterizing an agent, comprising:
treating a culture of eukaryotic cells comprising a DEL selection marker with an agent ("treated portion") or without an agent ("untreated portion");
measuring the mitochondrial activity of the treated portion of the cell culture in the presence of a suitable selection medium;
measuring the mitochondrial activity of the untreated portion of the cell culture in the presence of said selection medium; and
quantitating the change in mitochondrial activity and DEL induction between the treated portion and the untreated portions of the cell culture, wherein the change in mitochondrial activity and DEL induction indicates in a simultaneous manner both the cytotoxicity and mutagenicity of the agent;
wherein the eukaryotic cells comprise a construct having an auxotrophic gene disrupted by a colorigenic enzyme gene, and the colorigenic enzyme gene is disrupted by a polynucleotide encoding a selectable marker.

2. The method of claim 1, wherein the mitochondrial activity is measured by detecting the reduction of MTT or MTS.

3. The method of claim 1, wherein the cell culture comprises a cell selected from the group consisting of a mammalian lymphoid cell; a human lymphoblastoid cell; and a yeast cell.

4. A method of claim 3, wherein the cell culture comprises *Saccharomyces cerevisiae*.

5. The method of claim 1, wherein the measuring comprises detecting a colorimetric precipitate.

6. The method of claim 1, wherein the method is performed in a multi-well plate.

7. The method of claim 1, wherein the DEL selection marker is a metabolic enzyme or pathway.

8. The method of claim 1, wherein the DEL selection marker is an anti-microbial resistance gene.

9. The method of claim 1, wherein the DEL selection marker is the his gene.

10. The method of claim 1, wherein the auxotrophic gene comprises a His3 gene and the selectable marker comprises a Ura3 gene.

11. The method of claim 1, wherein the construct comprises a plasmid.

12. The method of claim 1, wherein the colorigenic enzyme gene comprises LacZ.

13. The method of claim 1, wherein the construct comprises the nucleic acid sequence set forth in SEQ ID NO: 1.

14. A method of screening an agent of mutagenic potential, comprising:
providing a cell culture comprising a plurality of micro-titer wells each well comprising a cell, each cell having a DEL selectable marker;
culturing a fraction of the cells with medium comprising an agent to be tested for mutagenicity and culturing a fraction of the cells with control medium;
washing the cells;
culturing the cells with an agent that measures mitochondrial activity; and
measuring a detectable signal indicative of mitochondrial activity;
wherein the cells are eukaryotic cells that comprise a construct having an auxotrophic gene disrupted by a colorigenic enzyme gene, and the colorigenic enzyme gene is disrupted by a polynucleotide encoding a selectable marker.

15. The method of claim 14, wherein the cell is a yeast cell.

16. The method of claim 14, wherein the agent is MTT or MTS.

17. The method of claim 14, wherein the detectable signal is a colorimetric signal and the measuring is by absorbance.

18. The method of claim 14, wherein the micro-titer wells are in a 96 or 384 well format.

* * * * *

SEQUENCE LISTING

```
<160> NUMBER OF SEQ ID NOS: 1

<210> SEQ ID NO 1
<211> LENGTH: 5243
<212> TYPE: DNA
<213> ORGANISM: Artificial Sequence
<220> FEATURE:
<223> OTHER INFORMATION: Vector Construct

<400> SEQUENCE: 1
atgacagagc agaaagccct agtaaagcgt attacaaatg aaaccaagat tcagattgcg      60
atctctttaa agggtggtcc cctagcgata gagcactcga tcttcccaga aaaagaggca     120
gaagcagtag cagaacaggc cacacaatcg caagtgatta acgtccacac aggtataggg     180
tttctggacc atatgataca tgctctggcc aagcattccg gctggtcgct aatcgttgag     240
tgcattggtg acttacacat agacgaccat cacaccactg aagactgcgg gattgctctc     300
```

```
ggtcacggat tagaagccgc cgagcgggcg acagccctcc gacggaagac tctcctccgt    360
gcgtcctcgt cttcaccggt cgcgttcctg aaacgcagat gtgcctcgcg ccgcactgct    420
ccgaacaata aagattctac aatactagct tttatggtta tgaagaggaa aaattggcag    480
taacctggcc ccacaaacct tcaaattaac gaatcaaatt aacaaccata ggatgataat    540
gcgattagtt ttttagcctt atttctgggg taattaatca gcgaagcgat gattttgat     600
ctattaacag atatataaat ggaaaagctg cataaccact ttaactaata ctttcaacat    660
tttcagtttg tattacttct tattcaaatg tcataaaagt atcaacaaaa aattgttaat    720
atacctctat actttaacgt caaggagaaa aaactataat gactaaatct cattcagaag    780
aagtgattgt acctgagttc aattctagcg caaaggaatt accaagacca ttggccgaaa    840
agtgcccaag cttaatcact agaggatccc cgggtaccga gctcgaattc caagctgatc    900
cggagcttgg ctgttgcccg tctcactggt gaaaagaaaa accaccctgg cgcccaatac    960
gcaaaccgcc tctccccgcg cgttggccga ttcattaatg cagctggcac gacaggtttc   1020
ccgacttaat cgccttgcag cacatccccc tttcgccagc tggcgtaata gcgaagaggc   1080
ccgcaccgat cgcccttccc aacagttgcg cagcctgaat ggcgaatggc gctttgcctg   1140
gtttccggca ccagaagcgg tgccggaaag ctggctggag tgcgatcttc ctgaggccga   1200
tactgtcgtc gtcccctcaa actggcagat gcacggttac gatgcgccca tctacaccaa   1260
cgtgacctat cccattacgg tcaatccgcc gtttgttccc acggagaatc cgacgggttg   1320
ttactcgctc acatttaatg ttgatgaaag ctggctacag gaaggccaga cgcgaattat   1380
ttttgatggc gttaactcgg cgtttcatct gtggtgcaac gggcgctggg tcggttacgg   1440
ccaggacagt cgtttgccgt ctgaatttga cctgagcgca ttttttacgcg ccggagaaaa   1500
ccgcctcgcg gtgatggtgc tgcgctggag tgacggcagt tatctggaag atcaggatat   1560
gtggcggatg agcggcattt tccgtgacgt ctcgttgctg cataaaccga ctacacaaat   1620
cagcgatttc catgttgcca ctcgctttaa tgatgatttc agccgcgctg tactggaggc   1680
tgaagttcag atgtgcggcg agttgcgtga ctacctacgg gtaacagttt ctttatggca   1740
gggtgaaacg caggtcgcca gcggcaccgc gcctttcggc ggtgaaatta tcgatgagcg   1800
tggtggttat gccgatcgcg tcacactacg tctgaacgtc gaaaacccga actgtggag    1860
cgccgaaatc ccgaatctct atcgtgcggt ggttgaactg cacaccgccg acggcacgct   1920
gattgaagca gaagcctgcg atgtcggttt ccgcgaggtg cggattgaaa atggtctgct   1980
gctgctgaac ggcaagccgt tgctgattcg aggcgttaac cgtcacgagc atcatcctct   2040
gcatggtcag gtcatggatg agcagacgat ggtgcaggat ttcaattcaa ttcatcattt   2100
ttttttttatt cttttttttg atttcggttt ctttgaaatt tttttgattc ggtaatctcc   2160
gaacagaagg aagaacgaag gaaggagcac agacttagat tggtatatat acgcatatgt   2220
agtgttgaag aaacatgaaa ttgcccagta ttcttaaccc aactgcacag aacaaaaacc   2280
tgcaggaaac gaagataaat catgtcgaaa gctacatata aggaacgtgc tgctactcat   2340
cctagtcctg ttgctgccaa gctatttaat atcatgcacg aaaagcaaac aaacttgtgt   2400
gcttcattgg atgttcgtac caccaaggaa ttactggagt tagttgaagc attaggtccc   2460
aaaatttgtt tactaaaaac acatgtggat atcttgactg attttccat ggagggcaca    2520
gttaagccgc taaaggcatt atccgccaag tacaatttt tactcttcga agacagaaaa    2580
tttgctgaca ttggtaatac agtcaaattg cagtactctg cgggtgtata cagaatagca   2640
```

```
gaatgggcag acattacgaa tgcacacggt gtggtgggcc caggtattgt tagcggtttg    2700
aagcaggcgg cagaagaagt aacaaaggaa cctagaggcc ttttgatgtt agcagaattg    2760
tcatgcaagg gctccctatc tactggagaa tatactaagg gtactgttga cattgcgaag    2820
agcgacaaag atttttgttat cggctttatt gctcaaagag acatgggtgg aagagatgaa    2880
ggttacgatt ggttgattat gacacccggt gtgggtttag atgacaaggg agacgcattg    2940
ggtcaacagt atagaaccgt ggatgatgtg gtctctacag gatctgacat tattattgtt    3000
ggaagaggac tatttgcaaa gggaagggat gctaaggtag agggtgaacg ttacagaaaa    3060
gcaggctggg aagcatattt gagaagatgc ggccagcaaa actaaaaaac tgtattataa    3120
gtaaatgcat gtatactaaa ctcacaaatt agagcttcaa tttaattata tcagttatta    3180
cccatcctgc tgatgaagca gaacaacttt aacgccgtgc gctgttcgca ttatccgaac    3240
catccgctgt ggtacacgct gtgcgaccgc tacggcctgt atgtggtgga tgaagccaat    3300
attgaaaccc acggcatggt gccaatgaat cgtctgaccg atgatccgcg ctggctaccg    3360
gcgatgagcg aacgcgtaac gcgaatggtg cagcgcgatc gtaatcaccc gagtgtgatc    3420
atctggtcgc tggggaatga atcaggccac ggcgctaatc acgacgcgct gtatcgctgg    3480
atcaaatctg tcgatccttc ccgcccggtg cagtatgaag gcggcggagc cgacaccacg    3540
gccaccgata ttatttgccc gatgtacgcg cgcgtggatg aagaccagcc cttcccggct    3600
gtgccgaaat ggtccatcaa aaaatggctt tcgctacctg gagagacgcg cccgctgatc    3660
ctttgcgaat acgcccacgc gatgggtaac agtcttggcg gtttcgctaa atactggcag    3720
gcgtttcgtc agtatccccg tttacagggc ggcttcgtct gggactgggt ggatcagtcg    3780
ctgattaaat atgatgaaaa cggcaacccg tggtcggctt acggcggtga ttttggcgat    3840
acgccgaacg atcgccagtt ctgtatgaac ggtctggtct ttgccgaccg cacgccgcat    3900
ccagcgctga cggaagcaaa acaccagcag cagttttttcc agttccgttt atccgggcaa    3960
accatcgaag tgaccagcga ataccctgttc cgtcatagcg ataacgagct cctgcactgg    4020
atggtggcgc tggatggtaa gccgctggca agcggtgaag tgcctctgga tgtcgctcca    4080
caaggtaaac agttgattga actgcctgaa ctaccgcagc cggagagcgc cgggcaactc    4140
tggctcacag tacgcgtagt gcaaccgaac gcgaccgcat ggtcagaagc cgggcacatc    4200
agcgcctggc agcagtggcg tctggcggaa aacctcagtg tgacgctccc cgccgcgtcc    4260
cacgccatcc gcatctgac caccagcgaa atggattttt gcatcgagct gggtaataag    4320
cgttggcaat taaccgcca gtcaggcttt ctttcacaga tgtggattgg cgataaaaaa    4380
caactgctga cgccgctgcg cgatcagttc accgtgcac cgctggataa cgacattggc    4440
gtaagtgaag cgacccgcat tgaccctaac gcctgggtcg aacgctggaa ggcggcgggc    4500
cattaccagg ccgaagcagc gttgttgcag tgcacggcag atacacttgc tgatgcggtg    4560
ctgattacga ccgctcacgc gtggcagcat caggggaaaa ccttatttat cagccggaaa    4620
acctaccgga ttgatggtag tggtcaaatg gcgattaccg ttgatgttga agtggcgagc    4680
gatacaccgc atccggcgcg gattggcctg aactgccagc tggcgcaggt agcagagcgg    4740
gtaaactggc tcggattagg gccgcaagaa aactatcccg accgccttac tgccgcctgt    4800
tttgaccgct gggatctgcc attgtcagac atgtataccc cgtacgtctt cccgagcgaa    4860
aacggtctgc gctgcgggac gcgcgaattg aattatggcc acaccagtg gcgcggcgac    4920 ttccagttca acatcagccg ctacagtcaa cagcaactga tggaaccag ccatcgccat    4980 ctgctgcacg cggaagaagg cacatggctg aatatcgacg gtttccatat ggggattggt    5040
```

```
ggcgacgact cctggagccc gtcagtatcg gcggaattag ctttgcagag gctagcagaa    5100
ttaccctcca cgttgattgt ctgcgaggca agaatgatca tcaccgtagt gagagtgcgt    5160
tcaaggctct tgcggttgcc ataagagaag ccacctcgcc caatggtacc aacgatgttc    5220
cctccaccaa aggtgttctt atg                                            5243
```